US008931482B2

(12) United States Patent
Hansmann et al.

(10) Patent No.: US 8,931,482 B2
(45) Date of Patent: Jan. 13, 2015

(54) BREATHING APPARATUS WITH COMPENSATION OF THE AMBIENT PRESSURE

(75) Inventors: Hans-Ullrich Hansmann, Barnitz (DE); Björn Petersen, Berlin (DE); Thomas Pernot, Lübeck (DE); Sandra Dankertt, Wesenberg (DE); Lutz Rüffert, Scharbeutz (DE); Marcus Romba, Lübeck (DE)

(73) Assignee: Draeger Safety AG & Co. KGaA, Luebeck (DE)

( * ) Notice: Subject to any disclaimer, the term of this patent is extended or adjusted under 35 U.S.C. 154(b) by 634 days.

(21) Appl. No.: 13/179,771

(22) Filed: Jul. 11, 2011

(65) Prior Publication Data

US 2012/0017906 A1 Jan. 26, 2012

(30) Foreign Application Priority Data

Jul. 21, 2010 (DE) ......................... 10 2010 031 754

(51) Int. Cl.

*F16K 31/02* (2006.01)
*A61M 15/00* (2006.01)
*A61M 16/00* (2006.01)
*A62B 18/00* (2006.01)
*A62B 7/10* (2006.01)

(52) U.S. Cl.

CPC ................. *A62B 18/006* (2013.01); *A62B 7/10* (2013.01)
USPC ............. 128/204.21; 128/200.24; 128/204.18

(58) Field of Classification Search

None
See application file for complete search history.

(56) References Cited

U.S. PATENT DOCUMENTS 5,816,870 A * 10/1998 Rubin ................................ 440/6
5,878,744 A * 3/1999 Pfeiffer ..................... 128/204.23
6,164,276 A * 12/2000 Bathe et al. .............. 128/202.22

(Continued)

FOREIGN PATENT DOCUMENTS

DE 203 20 369 U1 6/2004
EP 0 518 538 A2 12/1992
GB 2472592 A 2/2011

OTHER PUBLICATIONS

Combined search and examination report of the British Intellectual Property Office dated Jul. 26, 2011 for parallel British application GB1104903.8. in English.

*Primary Examiner* — Tan-Uyen (Jackie) T Ho
*Assistant Examiner* — Eric Bryant
(74) *Attorney, Agent, or Firm* — Walter Ottesen P.A.

(57) ABSTRACT

A breathing apparatus includes a filter, a motor and a blower driven by the motor. The filter is disposed ahead of the blower and the blower is configured to generate an air volume flow over the filter. A data storage unit has calibration curves for the air volume flow stored therein and the calibration curves are provided in characteristic line fields referenced to a known ambient pressure ($p_0$, $p_1$). Each of the characteristic line fields has a reference calibration curve referred to a predetermined operating state. A control unit is connected to the motor and the data storage unit. The control unit is configured to extrapolate one of the characteristic line fields for the operation of the motor by comparing a calibration curve ($\dot{V}_{ox}$) for an unknown ambient pressure ($p_x$) recorded at a predetermined operating state with a reference calibration curve.

9 Claims, 7 Drawing Sheets

(56) References Cited

U.S. PATENT DOCUMENTS

| | | | | |
|---|---|---|---|---|
| 6,302,106 | B1 * | 10/2001 | Lewis | 128/204.22 |
| 6,462,494 | B1 | 10/2002 | Schoene et al. | |
| 7,244,106 | B2 | 7/2007 | Kallman et al. | |
| 2004/0254495 | A1 * | 12/2004 | Mabary et al. | 600/547 |
| 2008/0127979 | A1 * | 6/2008 | Becker et al. | 128/205.27 |
| 2009/0266361 | A1 | 10/2009 | Bilger et al. | |
| 2011/0114094 | A1 * | 5/2011 | Stone et al. | 128/204.22 |

* cited by examiner

BREATHING APPARATUS WITH COMPENSATION OF THE AMBIENT PRESSURE

CROSS REFERENCE TO RELATED APPLICATION

This application claims priority of German patent application No. 10 2010 031 754.3, filed Jul. 21, 2010, the entire contents of which is incorporated herein by reference.

FIELD OF THE INVENTION

The invention relates to a breathing apparatus having a blower driven by a motor for the conveyance of an air volume flow over filters which are upstream of the blower.

BACKGROUND OF THE INVENTION

A breathing apparatus of this type is disclosed in United States patent application publication 2008/0127979 A1. Ambient air is drawn in via a filter upstream of the blower and conveyed to a hood or a breathing mask via a hose. The filter serves to filter out pollutants present in the ambient air. Multiple filters are normally operated in parallel to provide sufficient fresh breathing air. Because the filter resistance changes during the course of use, the blower is operated with previously measured characteristic lines with which the filter resistance can be estimated and a predetermined output for the volume flow can be set. As a result of the breathing air flow, a certain excess pressure develops in the hood or the breathing mask, which prevents the infiltration of harmful gases into the breathing air, and the breathing air flow must be set so that sufficient carbon dioxide can be flushed out. Typically, a breathing air flow of approximately 135 l/min is used.

The characteristic lines stored in the known breathing apparatus correspond to the circumstances during calibration and the ambient conditions during calibration. The temperature and the ambient pressure are important parameters. Because the known breathing apparatus can be used at different elevations, the density of the air drawn in changes and thus the blower output changes.

In a breathing apparatus known from United States patent application publication 2009/0266361 A1, it is suggested to determine the ambient pressure with a pressure sensor, to supply the measured value to the motor control and to incorporate it into the control of the motor. This requires an additional pressure sensor which needs to be monitored and maintained.

SUMMARY OF THE INVENTION

It is an object of the invention to provide an improved breathing apparatus which takes the influence of the ambient pressure into account in a simple manner and to provide a method for compensation of the ambient pressure influence.

The breathing apparatus of the invention includes: a filter; a motor; a blower driven by the motor and the filter being disposed ahead of the blower; the blower being configured to generate an air volume flow over the filter; a data storage unit having calibration curves for the air volume flow stored therein; the calibration curves being provided in characteristic line fields referenced to a known ambient pressure ($p_0$, $p_1$); each of the characteristic line fields having a reference calibration curve referred to a predetermined operating state; a control unit connected to the motor and the data storage unit; and, the control unit being configured to extrapolate one of the characteristic line fields for the operation of the motor by comparing a calibration curve ($\dot{V}_{ox}$) for an unknown ambient pressure ($p_x$) recorded at a predetermined operating state with a reference calibration curve.

According to the invention, calibration curves are recorded for predetermined values of the ambient pressure and these are stored in a memory of the breathing apparatus in the form of characteristic line fields relating to the ambient pressure. Predetermined values for the ambient pressure can, for example, be set in a vacuum chamber, and the calibration curves can be the revolutions per minute (n) of the motor in dependence of the motor current I for respective constant values of the volume flow generated by the blower. Additionally, the volume flow is a function of the filter resistance R. Each characteristic line field relating to a specific ambient pressure includes a calibration reference characteristic line related to a predetermined, defined operating state. This operating state can involve that the blower is operated with closed filters or that ambient air is drawn in via a calibration diaphragm.

Starting from a standard air pressure of 1013 hPa, the characteristic line field can be inputted in increments of approximately 50 hPa. Increasing air pressure is detected in single increments of 50 hPa and decreasing air pressure is detected in increments up to 70% of the standard air pressure. Preferably, characteristic line fields for representative values of the air pressure are recorded, such as 700, 850 and 1200 hPa, and the measured differences are described as a mathematical function in the form of a straight line equation. The characteristic line for the revolutions per minute (n) as a function of the motor current I can generally be represented in the form:

$$n=m*I+b$$

wherein m and b provide the slope and the axis intercept as a function of the air pressure. The measured curves are mathematically approximated by a straight line. The advantage of describing the dependence with a mathematical function is that intermediate values can be indicated with a formula even when there are no measurements for the intermediate values. It has been shown that calibration curves must be recorded only for a production lot, and an individual, apparatus-specific calibration is not required.

The compensation of the ambient pressure influence is effected in the following manner:

When the ambient pressure is unknown, a calibration curve which relates to the predetermined operating state is initially recorded. By comparing this calibration curve with the reference calibration curves previously recorded and stored in the data storage, the characteristic line field is calculated from the known values stored in the data storage, using the previously determined calculation formulas for the measured reference calibration curve at the unknown ambient pressure. This calculated character line field is subsequently used for the control of the motor.

A revolution counter for determining the revolutions per minute (n) of the drive shaft of the motor and an ammeter for determining the motor current I are provided for the recording of the calibration curves. The calibration curves include curves for constant volume flow ($\dot{V}_1$, $\dot{V}_2$, $\dot{V}_3$) as a function of the revolutions per minute (n) on the motor current I, n=f(I) in dependence on flow resistance R of the filters and the air pressure ($p_0$, $p_1$).

The method according to the invention for the compensation of the influence of the ambient pressure on the generation of the air volume flow in a breathing apparatus, which has a motor-driven blower and a filter upstream of the blower, includes the steps of:

recording characteristic line fields for the volume flow generated by the blower for predetermined values of the ambient pressure and storing these in a data storage of the breathing apparatus, in which connection each characteristic line field has a reference calibration curve relating to a predetermined operating state;

recording a calibration curve ($\dot{V}_{ox}$) for an unknown ambient pressure, which curve relates to a predetermined operating state;

extrapolating a characteristic line field for the operation of the motor from the characteristic line fields corresponding to the reference calibration curve on the basis of the calibration curve ($\dot{V}_{ox}$) recorded for the unknown ambient pressure.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
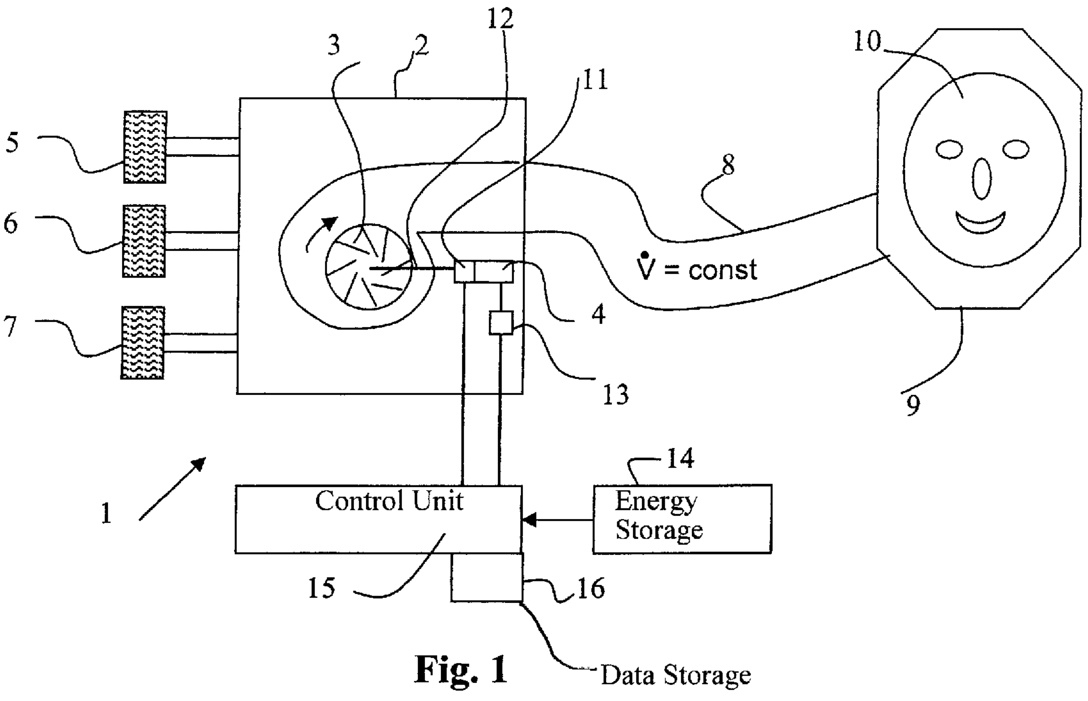
FIG. 1 shows the configuration of a breathing apparatus according to the invention.

FIG. 1 schematically shows a breathing apparatus 1 in which a blower 3 with a motor 4 is arranged in an apparatus housing 2, and ambient air is drawn in by the blower 3 via a parallel arrangement of three filters (5, 6, 7). The conveyed breathing gas is conveyed via a hose 8 to a head piece 9 which surrounds the head 10 of a wearer of the apparatus who is not shown in detail. The motor 4 is provided with an rpm counter 11, which detects the rpm (n) of the drive shaft 12, and an ammeter 13 detects the motor current I. An energy storage 14 supplies the energy required to operate the motor 4. A predetermined volume flow of 140 l/min to 240 l/min is set via a control unit 15 which is connected to the rpm counter 11, the ammeter 13 and the energy storage 14. The control unit 15 has a data storage 16 for the storage of characteristic lines ($\dot{V}_1$, $\dot{V}_2$, $\dot{V}_3$). Each characteristic line is analyzed and mathematically approximated by a straight line so that a functional correlation results between the rpm (n) and the motor current I.

Figure 2:
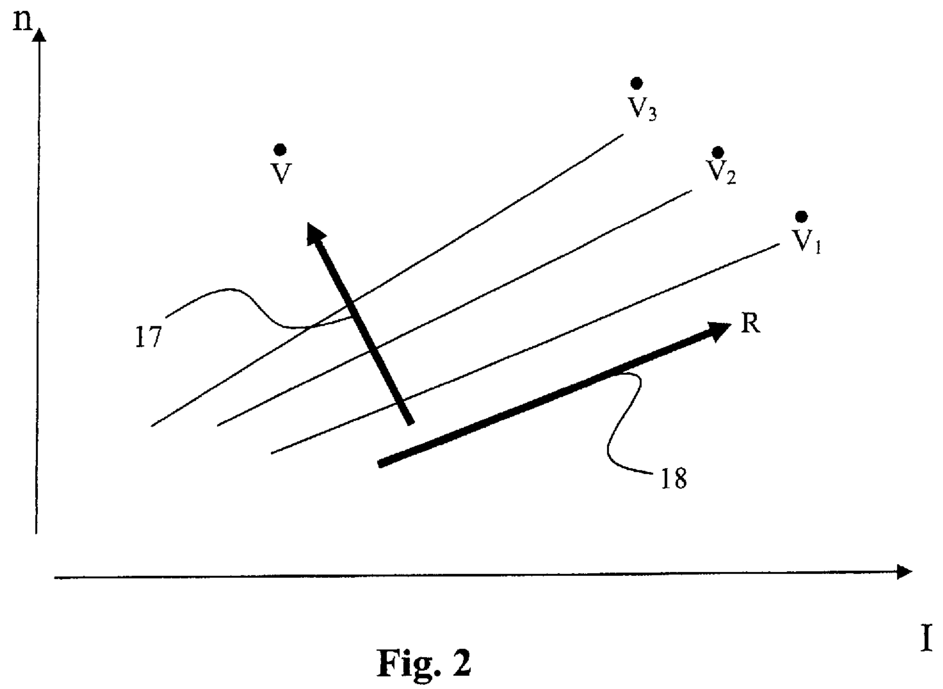
FIG. 2 is a schematic of a characteristic line field.

FIG. 2, as an example, shows a characteristic line field for the breathing apparatus 1 of FIG. 1. The motor current I is recorded on the abscissa and the rpm (n) on the ordinate in dependence on the filter resistance R and for constant volume flows ($\dot{V}_1$, $\dot{V}_2$, $\dot{V}_3$) wherein $\dot{V}_1<\dot{V}_2<\dot{V}_3$. The arrows (17, 18) for $\dot{V}$ and R represent increasing volume flows $\dot{V}$ and increasing filter resistances R, respectively. The characteristic lines shown in FIG. 2 enable the regulation of the volume flow $\dot{V}$ independently of the filter resistance R. The motor current I is available directly as a variable for the drive of the motor 4. However, no changes in the ambient conditions, for example, changing the air pressure, can be compensated with the characteristic lines ($\dot{V}_1$, $\dot{V}_2$, $\dot{V}_3$).

Figure 3:
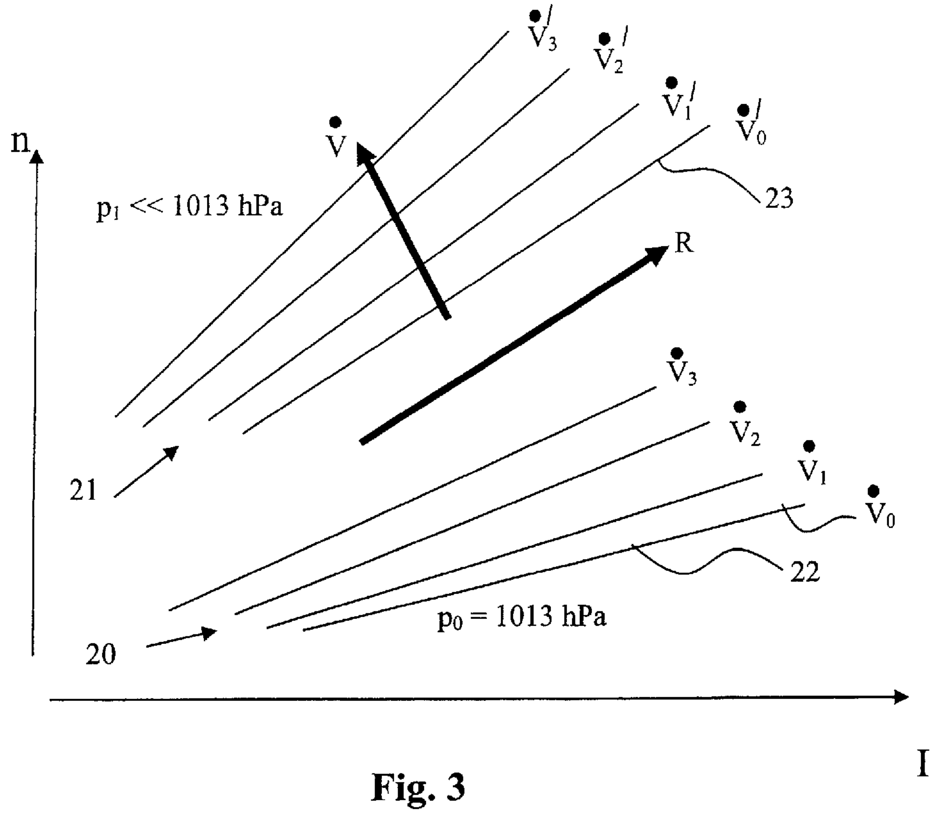
FIG. 3 shows the characteristic line field of FIG. 2 for two values of the ambient pressure.
Figure 4:
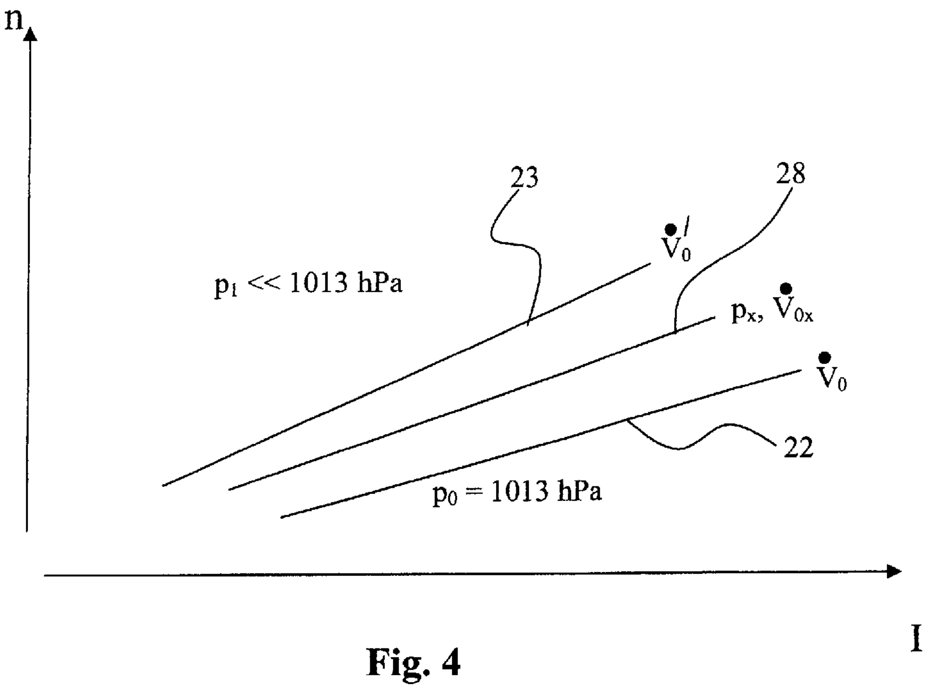
FIG. 4 shows reference calibration curves for characteristic line fields of FIG. 3.

FIG. 3 shows a first characteristic line field 20 for the volume flows ($\dot{V}_1$, $\dot{V}_2$, $\dot{V}_3$, $\dot{V}_1'$, $\dot{V}_2'$, $\dot{V}_3'$) for the normal air pressure $p_0$, of 1013 hPa and a second characteristic line field 21 with the volume flows ($\dot{V}_1'$, $\dot{V}_2'$, $\dot{V}_3'$) and the air pressure $p_1$ which is much less than the normal air pressure $p_0$. The two characteristic line fields (20, 21) additionally include characteristic lines 22, which corresponds to $\dot{V}_0$, and 23, which corresponds to $\dot{V}_0'$, and which were included as reference calibration curves with closed filters (5, 6, 7) with $\dot{V}=0$. These reference calibration curves (22, 23) with $\dot{V}_0=0$ for the air pressure $p_0$ and with $\dot{V}_0'=0$ for air pressure $p_1$, respectively, are shown in FIG. 4 in dependence on the rpm (n) and the motor current I. The curve 28 shows a characteristic line with $\dot{V}_{ox}=0$ for the unknown air pressure $p_x$.

Figure 5:
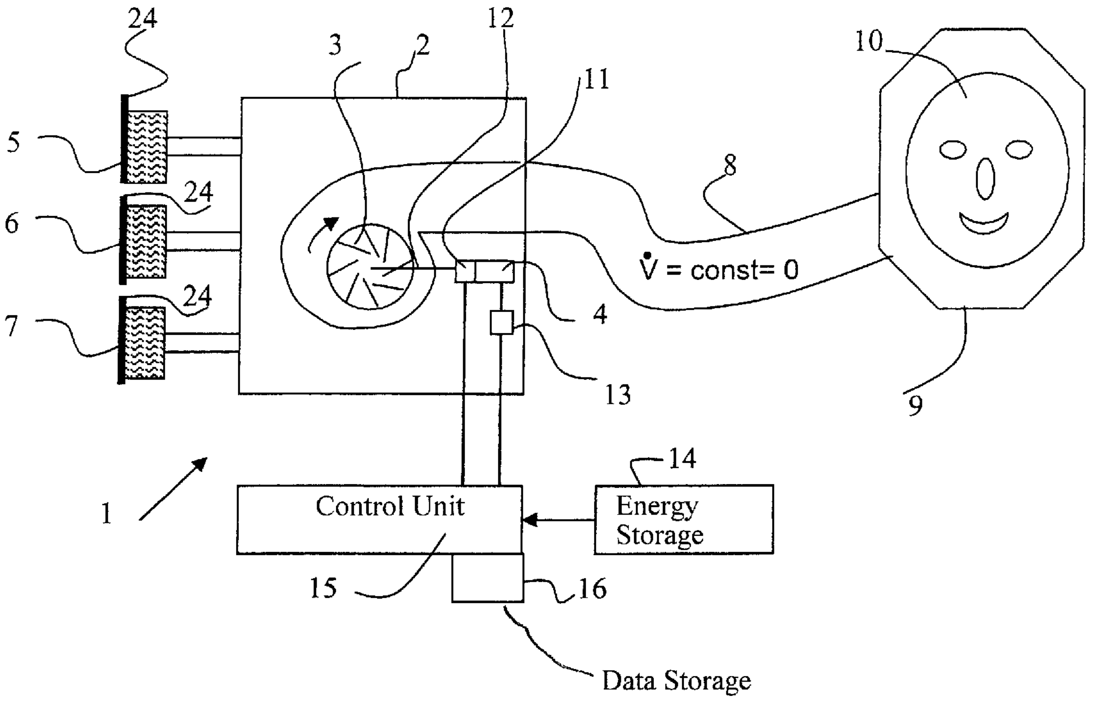
FIG. 5 shows the breathing apparatus of FIG. 1 with closed filters.

FIG. 5 shows the breathing apparatus 1 of FIG. 1 with closed filters (5, 6, 7) for receiving the reference calibration curves $\dot{V}_0$ and $\dot{V}_0'$. The gas inlet of the filters (5, 6, 7) is closed via a flap 24.

Figure 6:
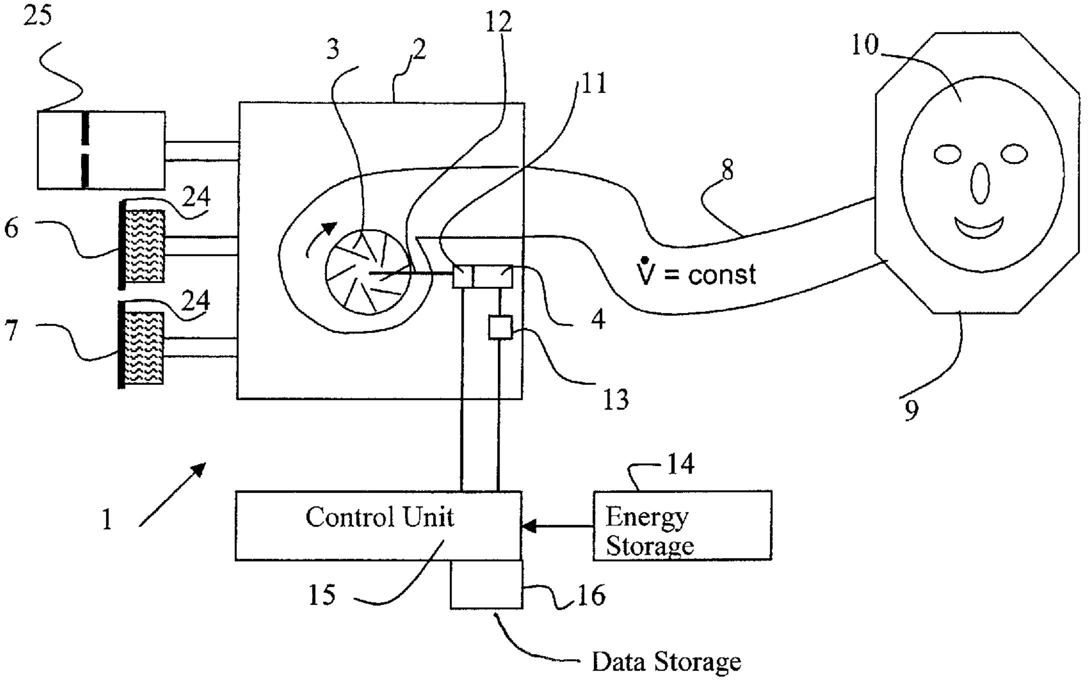
FIG. 6 shows the breathing apparatus of FIG. 5 with a calibration diaphragm.
Figure 7:
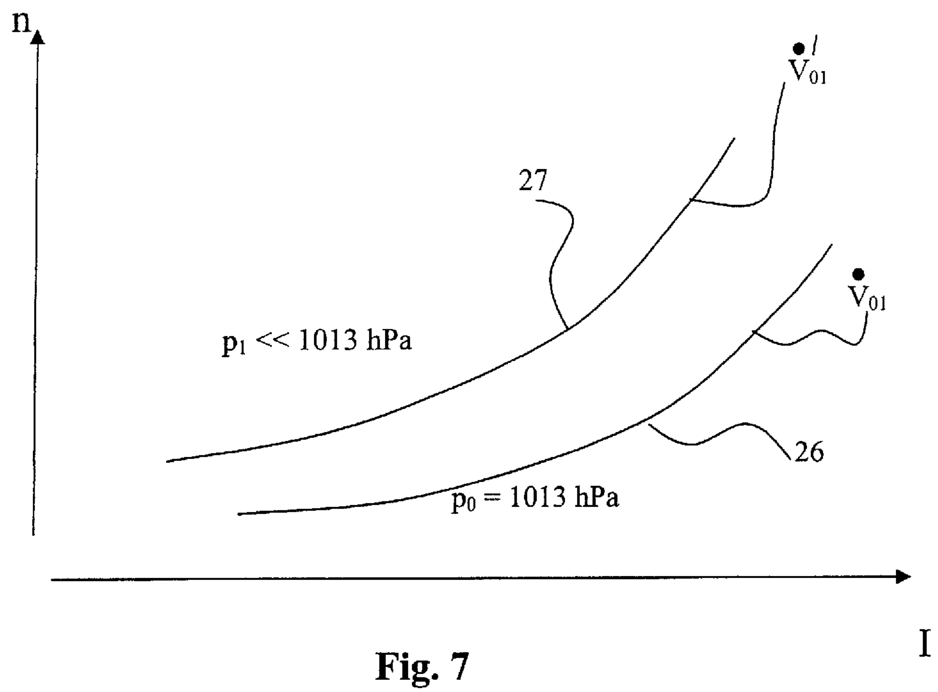
FIG. 7 shows reference calibration curves for the breathing apparatus of FIG. 6.

FIG. 6 shows the breathing apparatus of FIG. 1 wherein in contrast to the embodiment of FIG. 5, a calibration diaphragm 25 replaces the filter closed by the flap 24. Volume flows 26, $\dot{V}_{01}$ and 27, $\dot{V}_{01}'$ are moved via the calibration diaphragm 25 in dependence on the motor current I and the rpm (n) in dependence on the air pressure $p_0$ and $p_1$. The reference calibration curves (26, 27) present an alternative to the reference calibration curves (22, 23) with the volume flows $\dot{V}_0$ and $\dot{V}_0'$.

The compensation of the influence of the ambient pressure is effected in such a way that initially characteristic line fields $\dot{V}_1$, $\dot{V}_2$, $\dot{V}_3$, $\dot{V}_1'$, $\dot{V}_2'$, $\dot{V}_3'$ are recorded in a vacuum chamber for different values ($p_0$, $p_1$) of the ambient pressure. The curves $\dot{V}_0$ and $\dot{V}_0'$ thereby are reference calibration curves (22, 23) for the respective air pressure ($p_0$, $p_1$).

If the breathing apparatus 1 is operated at an unknown air pressure $p_x$, a calibration curve is initially recorded with closed filters (5, 6, 7) according to the apparatus of FIG. 5, or with the calibration diaphragm 25 according to FIG. 6. This is compared to the reference calibration curves stored in the data storage 16 and a characteristic line field for the control of the motor 4 is extrapolated from the characteristic line fields stored in the data storage 16 by means of mathematical calculation formulas.

It is assumed that the unknown air pressure is $p_x$. A calibration curve $\dot{V}_{ox}$, curve 28 in FIG. 4 is recorded with the breathing apparatus 1 according to FIG. 5, wherein the filters (5, 6, 7) are closed by a flap 24. The reference calibration curves (22, 23) with the associated characteristic line fields are approximated by mathematical calculation formulas in the form of straight line equations and as such are placed in the data storage 16. The corresponding characteristic line field for the regulation of the motor 4 can be determined via the calculation formula using the calibration curve $\dot{V}_{ox}$.

It is understood that the foregoing description is that of the preferred embodiments of the invention and that various changes and modifications may be made thereto without departing from the spirit and scope of the invention as defined in the appended claims.

REFERENCE NUMERAL LIST

1 breathing apparatus
2 apparatus housing
3 blower
4 motor
5, 6, 7 filter

8 hose
9 head piece
10 head
11 rpm counter
12 drive shaft
13 ammeter
14 energy storage
15 control unit
16 data storage
17 volume flow $\dot{V}$
18 filter resistance R
20 first characteristic line field
21 second characteristic line field
22 reference calibration curve $\dot{V}_0$
23 reference calibration curve $\dot{V}_0'$
24 flap
25 calibration diaphragm
26 volume flow $\dot{V}_{01}$
27 volume flow $\dot{V}_{01}'$
28 calibration curve $\dot{V}_{ox}$

What is claimed is:

1. A breathing apparatus comprising:
a filter;
a motor;
a blower driven by said motor and said filter being disposed ahead of said blower;
said blower being configured to generate an air volume flow over said filter;
a data storage unit having calibration curves for said air volume flow stored therein;
said calibration curves being provided in characteristic line fields referenced to a known ambient pressure;
each of said characteristic line fields having a reference calibration curve referred to a predetermined operating state;
a control unit connected to said motor and said data storage unit; and,
said control unit being configured to extrapolate one of said characteristic line fields to control said motor by comparing a calibration curve ($\dot{V}_{ox}$) for an unknown ambient pressure ($p_x$) recorded at a predetermined operating state with the reference calibration curve.

2. The breathing apparatus of claim 1, further comprising:
an rpm meter for detecting a rpm (n) of said motor;
an ammeter for detecting or a motor current (I); and,
said calibration curves recording said rpm (n) and said motor current (I).

3. The breathing apparatus of claim 1, wherein:
said filter has a flow resistance (R);
said calibration curves being provided for respective volume flows ($\dot{V}_1$, $\dot{V}_2$, $\dot{V}_3$, $\dot{V}_1'$, $\dot{V}_2'$, $\dot{V}_3'$) as respective functions of said rpm (n) on said motor current (I), and in dependence on said flow resistance (R) of said filter and said known ambient pressure.

4. The breathing apparatus of claim 1, wherein said predetermined operating state is a gas conveyance with said filters closed.

5. The breathing apparatus of claim 1, wherein said predetermined operating state is a gas conveyance via a calibration diaphragm.

6. A method for compensating for an influence of an ambient pressure on a conveyance of an air volume flow in a breathing apparatus which includes a blower driven by a motor and filters arranged upstream of the blower, the method comprising the steps of:
recording characteristic line fields for a volume flow ($\dot{V}_1$, $\dot{V}_2$, $\dot{V}_3$, $\dot{V}_1'$, $\dot{V}_2'$, $\dot{V}_3'$) conveyed by the blower at a known ambient pressure value;
storing the characteristic line fields in a data storage unit of the breathing apparatus wherein each of said characteristic line fields includes a reference calibration curve corresponding to a predetermined operating state;
recording a calibration curve ($\dot{V}_{ox}$) relating to said predetermined operating state at an unknown ambient pressure ($p_x$); and,
extrapolating a characteristic line field to control the motor based on said calibration curve ($\dot{V}_{ox}$) from the characteristic line fields corresponding to the reference calibration curve.

7. The method of claim 6, wherein said filters have a flow resistance (R) and the characteristic line fields for respective constant volume flows ($\dot{V}_1$, $\dot{V}_2$, $\dot{V}_3$, $\dot{V}_1'$, $\dot{V}_2'$, $\dot{V}_3'$) are determined as respective functions of an rpm (n) on a motor current (I), and in dependence on the flow resistance (R) of the filters and on a known air pressure.

8. The method of claim 6, wherein the predetermined operating state relates to a gas conveyance with closed filters.

9. The method of claim 6, wherein the predetermined operating state relates to a gas conveyance via a calibration diaphragm.

* * * * *

UNITED STATES PATENT AND TRADEMARK OFFICE

CERTIFICATE OF CORRECTION

PATENT NO. : 8,931,482 B2
APPLICATION NO. : 13/179771
DATED : January 13, 2015
INVENTOR(S) : H. Hansmann et al.

It is certified that error appears in the above-identified patent and that said Letters Patent is hereby corrected as shown below:

On the Title Page:
Under (75) Inventors: delete "Sandra Dankertt" and substitute -- Sandra Dankert -- therefor.

In the Specification:
In column 4:
Line 5: delete " $\left(\dot{V}_1, \dot{V}_2, \dot{V}_3; \dot{V}_1', \dot{V}_2', \dot{V}_3'\right)$ " and substitute -- $\left(\dot{V}_1, \dot{V}_2, \dot{V}_3\right)$ -- therefor.

Signed and Sealed this
Twenty-third Day of June, 2015

Michelle K. Lee
*Director of the United States Patent and Trademark Office*